United States Patent
O'Mahony

(10) Patent No.: US 10,052,425 B2
(45) Date of Patent: Aug. 21, 2018

(54) RESERVOIR STATUS LIGHTS INDICATING STATUS OF CORRESPONDING RESERVOIRS FOR EXTRACORPOREAL BLOOD TREATMENT APPARATUS

(71) Applicant: GAMBRO LUNDIA AB, Lund (SE)

(72) Inventor: John O'Mahony, Maple Grove, MN (US)

(73) Assignee: Gambro Lundia AB, Lund (SE)

( * ) Notice: Subject to any disclaimer, the term of this patent is extended or adjusted under 35 U.S.C. 154(b) by 68 days.

(21) Appl. No.: 14/774,004

(22) PCT Filed: Mar. 14, 2014

(86) PCT No.: PCT/US2014/027463
§ 371 (c)(1),
(2) Date: Sep. 9, 2015

(87) PCT Pub. No.: WO2014/152548
PCT Pub. Date: Sep. 25, 2014

(65) Prior Publication Data
US 2016/0022893 A1  Jan. 28, 2016

Related U.S. Application Data

(60) Provisional application No. 61/793,590, filed on Mar. 15, 2013.

(51) Int. Cl.
*G01F 23/20* (2006.01)
*G01G 17/04* (2006.01)
(Continued)

(52) U.S. Cl.
CPC ............ *A61M 1/1643* (2014.02); *A61M 1/14* (2013.01); *A61M 1/34* (2013.01); *A61M 1/367* (2013.01);
(Continued)

(58) Field of Classification Search
CPC ........ G01G 17/04; G01G 17/06; G01G 19/14; G01G 23/32; A61M 1/1643;
(Continued)

(56) References Cited

U.S. PATENT DOCUMENTS 3,389,387 A * 6/1968 Hulse ................ A61M 5/16845
128/DIG. 13
3,390,238 A * 6/1968 O'Neill ............. A61M 5/16845
128/DIG. 13
(Continued)

FOREIGN PATENT DOCUMENTS

EP         0522075        10/1991
EP         0276377         1/1992
(Continued)

OTHER PUBLICATIONS

PCT Preliminary Examination Report for PCT/US2014/027463 dated Sep. 24, 2015 (8 pages).
(Continued)

*Primary Examiner* — Randy Gibson
(74) *Attorney, Agent, or Firm* — Mueting, Raasch & Gebhardt, P.A.

(57) ABSTRACT

Extracorporeal blood treatment apparatus with reservoir status lights and methods of monitoring reservoir status using the same are described. The extracorporeal blood treatment apparatus include a plurality of reservoir scales (30), each of which is configured to weigh a reservoir (32) used in connection with the extracorporeal blood treatment apparatus. A plurality of reservoir status lights (40) are provided, with one or more of the reservoir status lights (40) associated with one of the reservoir scales (30). The one or more reservoir status lights (40) associated with one of the reservoir scales (30) emit light from a location that is closer
(Continued)

to their associated reservoir scale than to any other reservoir scale of the extracorporeal blood treatment apparatus.

25 Claims, 4 Drawing Sheets

(51) Int. Cl.
    *G01G 19/14*     (2006.01)
    *A61M 1/14*     (2006.01)
    *A61M 1/36*     (2006.01)
    *G01G 23/32*     (2006.01)
    *A61M 1/16*     (2006.01)
    *A61M 1/34*     (2006.01)

(52) U.S. Cl.
    CPC .............. *G01F 23/20* (2013.01); *G01G 19/14* (2013.01); *G01G 23/32* (2013.01); *A61M 2205/3306* (2013.01); *A61M 2205/3393* (2013.01); *A61M 2205/50* (2013.01); *G01G 17/04* (2013.01)

(58) Field of Classification Search
    CPC .. A61M 2205/3393; A61M 1/14; A61M 1/34; A61M 1/367; G01F 23/20; G01F 23/205
    See application file for complete search history.

(56) References Cited

U.S. PATENT DOCUMENTS

| | | | |
|---|---|---|---|
| 3,655,123 A | 4/1972 | Judson | |
| 3,977,567 A * | 8/1976 | Rudd | A61M 5/16845 128/DIG. 13 |
| 4,034,361 A * | 7/1977 | Mortensen | F17C 13/023 177/46 |
| 4,378,854 A * | 4/1983 | Rosen | A61M 1/024 177/118 |
| 4,559,036 A * | 12/1985 | Wunsch | A61M 5/16827 604/247 |
| 4,582,598 A * | 4/1986 | Bilstad | A61M 1/3496 210/101 |
| 4,977,850 A * | 12/1990 | King | A61M 1/024 116/109 |
| 4,994,026 A | 2/1991 | Fecondini | |
| 5,141,492 A * | 8/1992 | Dadson | A61M 1/28 604/28 |
| 5,769,087 A | 6/1998 | Westphal | |
| 7,891,625 B2 | 2/2011 | Chevallet | |
| 7,938,817 B2 | 5/2011 | Gelfand | |
| 8,262,602 B2 | 9/2012 | Lee | |
| 8,514,242 B2 * | 8/2013 | Luengen | G06F 3/14 345/207 |
| 8,730,050 B2 * | 5/2014 | Bregeon | A61G 7/0503 340/603 |
| 8,933,810 B1 * | 1/2015 | Donehue | G01F 23/74 340/618 |
| 2002/0032403 A1 | 3/2002 | Savagle | |
| 2004/0026134 A1 * | 2/2004 | Waggoner | G01G 19/62 177/160 |
| 2005/0056092 A1 * | 3/2005 | Kowalski | G01F 23/74 73/313 |
| 2005/0109105 A1 * | 5/2005 | Kowalski | G01F 23/74 73/313 |
| 2008/0027409 A1 | 1/2008 | Rudko | |
| 2010/0315231 A1 | 12/2010 | Rada | |
| 2015/0034538 A1 * | 2/2015 | Pouchoulin | A61M 1/16 210/141 |
| 2016/0038665 A1 * | 2/2016 | Schaefer | G06F 19/3406 137/551 |
| 2017/0209637 A1 * | 7/2017 | Schaefer | A61M 1/367 |

FOREIGN PATENT DOCUMENTS

| | | |
|---|---|---|
| EP | 0565585 | 7/1992 |
| EP | 1765435 | 12/2005 |
| WO | WO 97/10856 | 3/1997 |
| WO | WO 2004/064896 | 8/2004 |
| WO | WO 2005/101279 | 10/2005 |
| WO | WO 2009/131266 | 10/2009 |
| WO | WO 2012/108910 | 8/2012 |

OTHER PUBLICATIONS

PCT International Search Report and Written Opinion for PCT/US2014/027463 dated Jul. 10, 2014 (12 pages).

\* cited by examiner

RESERVOIR STATUS LIGHTS INDICATING STATUS OF CORRESPONDING RESERVOIRS FOR EXTRACORPOREAL BLOOD TREATMENT APPARATUS

CROSS-REFERENCE

This application is a U.S. National Stage Application of International Application No. PCT/US2014/027463, filed Mar. 14, 2014 and published in English on Sep. 25, 2014 as International Publication No. WO 2014/152548 A1, which claims the benefit under 35 U.S.C. 119(e) of U.S. Provisional Application Ser. No. 61/793,590, filed on Mar. 15, 2013, which are incorporated herein by reference in their entirety.

Extracorporeal blood treatment apparatus with reservoir status lights and methods of monitoring reservoir status using the same are described herein.

BACKGROUND

Extracorporeal blood treatment means taking the blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment is used with patients incapable of effectively eliminating matter from their blood, for example, in the case of a patient who is suffering from temporary or permanent kidney failure. These and other patients may undergo extracorporeal blood treatment to add to or to eliminate matter from their blood, to maintain an acid-base balance or to eliminate excess body fluids, for instance.

In a variety of extracorporeal blood treatments, one or more liquids may be supplied to the extracorporeal blood treatment apparatus for use during the treatments and one or more liquids may be collected as a part of the treatments. Both the supplied and collected liquids may be stored in one or more reservoirs. Those reservoirs may, during the course of treatment of a single patient, need to be replaced as they are either emptied (in the case of liquids supplied as a part of the treatment) or are filled to capacity (in the case of liquids collected as a part of the treatment).

Although many extracorporeal blood treatment apparatus include displays used to monitor the operation of the apparatus as well as the status of any reservoirs attached to the apparatus, those displays are typically physically remote from the reservoirs themselves. For example, in many extracorporeal blood treatment apparatus the reservoirs are provided in the form of bags that hang from the bottom of a housing containing the extracorporeal blood treatment apparatus, while displays are typically located higher on the machine so that they are closer to eye level for the user.

SUMMARY

Extracorporeal blood treatment apparatus with reservoir status lights and methods of monitoring reservoir status using the same are described herein. The extracorporeal blood treatment apparatus described herein include a plurality of reservoir scales, each of which is configured to weigh a reservoir used in connection with the extracorporeal blood treatment apparatus. In addition, a plurality of reservoir status lights are provided, with one or more of the reservoir status lights associated with one of the reservoir scales. Further, the one or more reservoir status lights associated with one of the reservoir scales emit light from a location that is closer to their associated reservoir scale than to any other reservoir scale of the extracorporeal blood treatment apparatus.

The reservoir status lights can, in one or more embodiments, be used to provide an indication of the status of a reservoir attached to the reservoir scale. In particular, the reservoir status light may provide an indication that a reservoir attached to a reservoir scale has passed a selected weight limit. That weight limit may, in the case of a reservoir used to collect liquids, be an upper limit such that passing the selected weight limit is an indication that the reservoir is reaching its capacity and may need to be replaced with a reservoir having more capacity to collect liquid. In the case of a reservoir used to supply liquids, the weight limit may be a lower limit such that passing the selected weight limit is an indication that the reservoir is reaching a level at which the reservoir may need to be replaced with a fresh reservoir containing additional liquid to be supplied to the extracorporeal blood treatment apparatus.

The reservoir status lights may, in one or more embodiments, also be used to provide an indication of the status of the reservoir scale (i.e., whether the reservoir scale is in a loading position or an operating position).

Although the extracorporeal blood treatment apparatus may include a display to allow a user to monitor the status of reservoirs attached to the reservoir scales, the display is typically physically remote from the reservoir scales. As a result, a user is required to shift their attention between the display and the reservoir scales when identifying a reservoir scale having a reservoir that requires replacement. The reservoir status lights used in extracorporeal blood treatment apparatus as described herein may, however, allow the user to identify and/or replace reservoirs on the reservoir scales without requiring them to shift their attention away from the reservoir scales during the process.

In a first aspect, one or more embodiments of the extracorporeal blood treatment apparatus described herein may include: a housing comprising a front face and a bottom end; one or more pumps located on or in the housing, wherein the one or more pumps are configured to move blood and a treatment solution during extracorporeal blood treatment, wherein the one or more pumps are located above the bottom end of the housing; a plurality of reservoir scales positioned proximate the bottom end of the housing, wherein each reservoir scale of the plurality of reservoir scales is configured to weigh a reservoir operably attached to the reservoir scale, wherein the reservoir is positioned below the bottom end of the housing, and wherein the plurality of reservoir scales comprises at least a first reservoir scale and a second reservoir scale; a plurality of reservoir status lights, wherein each reservoir status light of the plurality of reservoir status lights is associated with one reservoir scale of the plurality of reservoir scales, and wherein the plurality of reservoir status lights comprises a first reservoir status light associated with the first reservoir scale and a second reservoir status light associated with the second reservoir scale, and further wherein the first reservoir status light emits light from a location that is closer to the first reservoir scale than the second reservoir scale; a control unit operably attached to the one or more pumps, the plurality of reservoir scales, and the plurality of reservoir status lights. In one or more embodiments, the control unit is configured to: receive a weight signal from each reservoir scale of the plurality of reservoir scales, wherein the weight signal from each reservoir scale is indicative of a weight of a reservoir operably attached to the reservoir scale; make a determination that a reservoir operably attached to the first reservoir scale has passed a first selected weight limit at least partially based on the weight signal received from the first reservoir scale; change a mode of light emitted by the first reservoir status light after making the determination that the first reservoir scale has passed the first selected weight limit; make a determination that a reservoir operably attached to the second reservoir scale has passed a second selected weight limit at least partially based on the weight signal received from the second reservoir scale; and change a mode of light emitted by the second reservoir status light after making the determination that the second reservoir scale has passed the second selected weight limit.

In one or more embodiments of the apparatus described herein, the first reservoir status light is located on the first reservoir scale and the second reservoir status light is located on the second reservoir scale.

In one or more embodiments of the apparatus described herein, the first reservoir status light is located on the housing proximate the first reservoir scale and the second reservoir status light is located on the housing proximate the second reservoir scale.

In one or more embodiments of the apparatus described herein, the first reservoir scale comprises a loading position in which the first reservoir scale is configured to receive a reservoir operably attached to the first reservoir scale, and an operating position in which the first reservoir scale is configured to weigh a reservoir operably attached to the first reservoir scale during operation of the extracorporeal blood treatment apparatus, and wherein the control unit is configured to cause the first reservoir status light to emit light in an operating mode when the first reservoir scale is in the operating position. In one or more embodiments, the control unit is configured to cause the first reservoir status light to emit light in a loading mode when the first reservoir scale is not in the operating position.

In one or more embodiments of the apparatus described herein, the control unit is configured to: make a determination that the weight of liquid in the reservoir operably attached to the first reservoir scale has not passed the first selected weight limit; cause the first reservoir status light to emit light of a first color when the weight of liquid in the reservoir operably attached to the first reservoir scale has not passed the first selected weight limit. In one or more embodiments, the control unit is configured to: make a determination that the weight of liquid in the reservoir operably attached to the second reservoir scale has not passed the second selected weight limit; cause the second reservoir status light to emit light of a second color when the weight of liquid in the reservoir operably attached to the second reservoir scale has not passed the second selected weight limit, wherein the first color and the second color are different colors. In one or more embodiments, the apparatus comprises a first passive color indicator on the first reservoir scale, wherein the first passive color indicator matches the first color emitted by the first reservoir status light when the weight of liquid in the reservoir operably attached to the first reservoir scale has not passed the first selected weight limit, and wherein the apparatus comprises a second passive color indicator on the second reservoir scale, wherein the second passive color indicator matches the second color emitted by the second reservoir status light when the weight of liquid in the reservoir operably attached to the second reservoir scale has not passed the second selected weight limit.

In one or more embodiments of the apparatus described herein, changing the mode of light emitted by the first reservoir status light after making the determination that the first reservoir scale has passed the first selected weight limit comprises causing the first reservoir status light to vary the intensity of light emitted by the first reservoir status light.

In one or more embodiments of the apparatus described herein, changing the mode of light emitted by the first reservoir status light after making the determination that the first reservoir scale has passed the first selected weight limit comprises causing the first reservoir status light to change the color of light emitted by the first reservoir status light.

In one or more embodiments of the apparatus described herein, changing the mode of light emitted by the second reservoir status light after making the determination that the second reservoir scale has passed the second selected weight limit comprises causing the second reservoir status light to vary the intensity of light emitted by the second reservoir status light.

In one or more embodiments of the apparatus described herein, changing the mode of light emitted by the second reservoir status light after making the determination that the second reservoir scale has passed the second selected weight limit comprises causing the second reservoir status light to change the color of light emitted by the second reservoir status light.

In one or more embodiments of the apparatus described herein, the apparatus comprises a display screen operably connected to the control unit and an ambient light sensor operably connected to the control unit, and wherein the control unit is configured to reduce the intensity of light emitted from the display screen when ambient light detected by the ambient light sensor is below a selected ambient light threshold.

In a second aspect, one or more embodiments of methods of monitoring reservoir status in an extracorporeal blood treatment apparatus are described herein, where the apparatus comprises one or more pumps located on or in a housing that are configured to move blood and a treatment solution during extracorporeal blood treatment, a first reservoir scale and a second reservoir scale positioned proximate a bottom end of the housing, and a first reservoir status light associated with the first reservoir scale and a second reservoir status light associated with the second reservoir scale. The methods may include: receiving a weight signal from the first reservoir scale, wherein the weight signal from the first reservoir scale is indicative of a weight of a reservoir operably attached to the first reservoir scale; determining that a reservoir operably attached to the first reservoir scale has passed a first selected weight limit at least partially based on the weight signal received from the first reservoir scale; changing a mode of light emitted by the first reservoir status light after determining that the first reservoir scale has passed the first selected weight limit, wherein the first reservoir status light emits light from a location that is closer to the first reservoir scale than the second reservoir scale; determining that a reservoir operably attached to the second reservoir scale has passed a second selected weight limit at least partially based on the weight signal received from the second reservoir scale; and changing a mode of light emitted by the second reservoir status light after determining that the second reservoir scale has passed the second selected weight limit.

In one or more embodiments of the methods described herein, the first reservoir scale comprises a loading position in which the first reservoir scale is configured to receive a reservoir operably attached to the first reservoir scale, and an operating position in which the first reservoir scale is configured to weigh a reservoir operably attached to the first reservoir scale during operation of the extracorporeal blood treatment apparatus, and the method further comprises: emitting light from the first reservoir status light in a loading mode when the first reservoir scale is not in the operating position; and emitting light from the first reservoir status light in an operating mode when the first reservoir scale is in the operating position, wherein the light emitted from the first reservoir status light in the loading mode differs from the light emitted from the first reservoir status light in the operating mode.

In one or more embodiments of the methods described herein, the first reservoir status light is located on the first reservoir scale and the second reservoir status light is located on the second reservoir scale.

In one or more embodiments of the methods described herein, the first reservoir status light is located on the housing proximate the first reservoir scale and the second reservoir status light is located on the housing proximate the second reservoir scale.

In one or more embodiments of the methods described herein, the method further comprises: determining that the weight of liquid in the reservoir operably attached to the first reservoir scale has not passed the first selected weight limit; and emitting light of a first color from the first reservoir status light of a first color when the weight of liquid in the reservoir operably attached to the first reservoir scale has not passed the first selected weight limit. In one or more embodiments, the method further comprises: determining that the weight of liquid in the reservoir operably attached to the second reservoir scale has not passed the second selected weight limit; and emitting light of a second color from the second reservoir status light when the weight of liquid in the reservoir operably attached to the second reservoir scale has not passed the second selected weight limit, wherein the first color and the second color are different colors. In one or more embodiments, the apparatus comprises a first passive color indicator on the first reservoir scale and a second passive color indicator on the second reservoir scale; wherein the light of the first color emitted by the first reservoir status light matches the first passive color indicator when the weight of liquid in the reservoir operably attached to the first reservoir scale has not passed the first selected weight limit; and wherein the light of the second color emitted by the second reservoir status light matches the second passive color indicator when the weight of liquid in the reservoir operably attached to the second reservoir scale has not passed the second selected weight limit.

In one or more embodiments of the methods described herein, changing the mode of light emitted by the first reservoir status light after determining that the first reservoir scale has passed the first selected weight limit comprises varying the intensity of light emitted by the first reservoir status light.

In one or more embodiments of the methods described herein, changing the mode of light emitted by the first reservoir status light after determining that the first reservoir scale has passed the first selected weight limit comprises changing the color of light emitted by the first reservoir status light.

In one or more embodiments of the methods described herein, changing the mode of light emitted by the second reservoir status light after determining that the second reservoir scale has passed the second selected weight limit comprises varying the intensity of light emitted by the second reservoir status light.

In one or more embodiments of the methods described herein, changing the mode of light emitted by the second reservoir status light after determining that the second reservoir scale has passed the second selected weight limit comprises changing the color of light emitted by the second reservoir status light.

In one or more embodiments of the methods described herein, the apparatus comprises a display screen and an ambient light sensor, and the method further comprises reducing the intensity of light emitted from the display screen when ambient light detected by the ambient light sensor is below a selected ambient light threshold.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the extracorporeal blood treatment apparatus and methods described herein. Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

Figure 1:
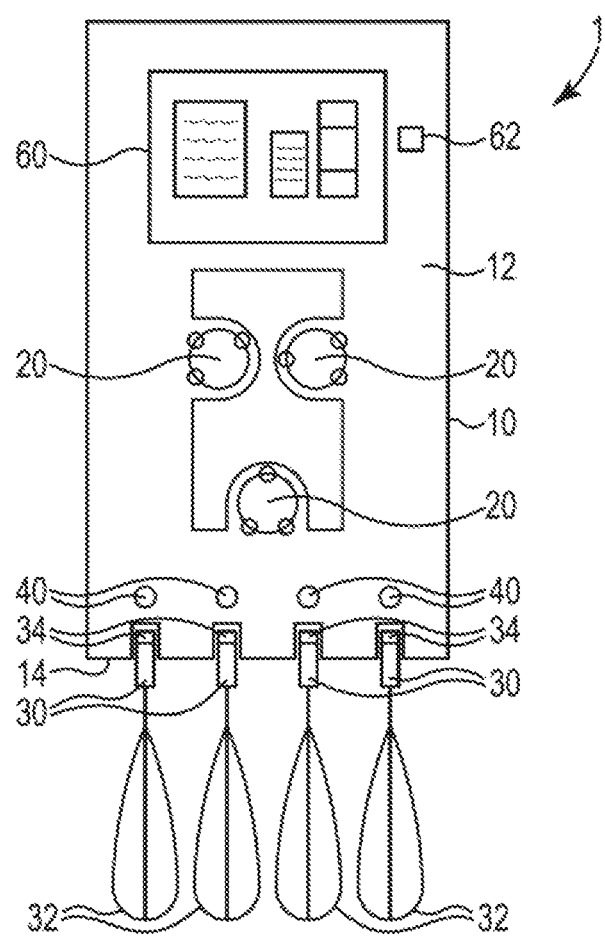
FIG. 1 depicts one illustrative embodiment of an extracorporeal blood treatment apparatus as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Referring to FIG. 1, one illustrative embodiment of an extracorporeal blood treatment apparatus 1 is depicted. The apparatus 1 includes a housing 10 having a front face 12. The apparatus further includes one or more pumps 20 used to move liquids through the apparatus as part of a treatment process. Although the pumps 20 are depicted in the form of peristaltic pumps, the pumps used in the extracorporeal blood treatment apparatus described herein may be provided in a variety of alternative forms, e.g., piston pumps, diaphragm pumps, etc.

The extracorporeal blood treatment apparatus 1 also includes, in one or more embodiments, a display 60 used to convey information to a user. The display 60 may also serve as an input device if, e.g., the display 60 is in the form of a touchscreen. Also, although the display 60 is depicted as being located in the housing 10, in one or more alternative embodiments, the display 60 may be separate from the housing 10 of the extracorporeal blood treatment apparatus 1.

The extracorporeal blood treatment apparatus 1 also includes reservoir scales 30, each of which is configured to hold and weigh a reservoir 32. The reservoir scales 30 are positioned below a bottom end 14 of the housing 10, at least in part because the reservoirs 32 are typically attached to and hang from the reservoir scales 30. Although the depicted embodiment of extracorporeal blood treatment apparatus 1 includes four reservoir scales 30 and associated reservoirs 32, alternative embodiments of an extracorporeal blood treatment apparatus as described herein may include as few as two reservoirs 30 and associated reservoirs 32. In still other variations, one of the reservoir scales 30 may be used to hold and weigh two or more reservoirs 32 rather than a single reservoir 32 as depicted in FIG. 1.

The reservoirs 32 may be in the form of, e.g., flexible polymeric bags configured to hold liquids, although the reservoirs 32 used in connection with the extracorporeal blood treatment apparatus described herein may take any suitable form in which liquids can be stored and weighed by reservoir scales 30, e.g., bottles, tanks, cartons, etc.

The extracorporeal blood treatment apparatus 1 depicted in FIG. 1 may also include passive color indicators 34 on each of the reservoir scales 30. The passive color indicators 34 may be used as a designation of the contents of each of the reservoirs 32 attached to the reservoir scale 30. For example, if one of the reservoirs 32 is connected to the extracorporeal blood treatment apparatus 1 to collect waste fluid from, e.g., a dialysis filter, the passive color indicator 34 associated with the reservoir scale 30 holding the waste reservoir 32 may have a selected color that is different than, e.g., a reservoir scale 30 holding a reservoir 32 that is used to supply dialysate liquid within the same extracorporeal blood treatment apparatus 1. The passive color indicators 34 used in connection with an extracorporeal blood treatment apparatus as described herein may be in the form of patches, stickers, paint, or any other suitable technique of displaying a color to a user of the extracorporeal blood treatment apparatus that does not involve emitting light. Although the passive color indicators 34 are depicted as being located on the reservoir scales 30, the passive color indicators 34 may, in one or more embodiments, be located on the housing 10, while in one or more other embodiments passive color indicators may be located on both the reservoir scales 30 and the housing 10.

A plurality of reservoir status lights 40 are also depicted in connection with the extracorporeal blood treatment apparatus 1 of FIG. 1 and may be used to monitor the status of the reservoirs 32 attached to the reservoir scales 30 associated with the reservoir status lights 40. In one or more embodiments, the reservoir status lights 40 are located below the one or more pumps 20 and the display 60 (if provided) of the extracorporeal blood treatment apparatus. Because, in one or more embodiments, the reservoirs 32 hang from the reservoir scales 30, the reservoir status lights 40 may be described as being located below the one or more pumps 20 and above the reservoirs 32 attached to the reservoir scales 30 of the extracorporeal blood treatment apparatus 1. Further, although the reservoir status lights 40 are depicted as being located on the front face 12 of the housing 10, the reservoir status lights 40 may, in one or more alternative embodiments, be provided on the reservoir scales 30 and/or on another surface of the extracorporeal blood treatment apparatus 1. In such an embodiment, one or more passive color indicators 34 associated with each of the reservoir scales 30 may be located on the housing 10 and/or on the reservoir scales 30.

Each of the reservoir status lights 40 is associated with only one reservoir scale 30 of the extracorporeal blood treatment apparatus. For example, a first reservoir status light 40 may be associated with a first reservoir scale 30, while a second reservoir status light 40 may be associated with a second reservoir scale 30. Although the depicted extracorporeal blood treatment apparatus 1 includes only one reservoir status light 40 associated with each reservoir scale 30, in one or more alternative embodiments, two or more reservoir status lights 40 may be associated with one reservoir scale 30.

Although the display 60 may be used to monitor the operation of the extracorporeal blood treatment apparatus 1 as well as the status of any reservoirs 32 attached to the reservoir scales 30, the display 60 is physically remote from the reservoirs 32 themselves. As a result, a user is required to shift their attention between the display 60 and the reservoir scales 30 when identifying a reservoir 32 that requires replacement using the display 60.

In the extracorporeal blood treatment apparatus described herein, however, the reservoir status lights 40 can, in one or more embodiments, be used to provide an indication of the status of a reservoir 32 attached to the reservoir scale 30 that is associated with a reservoir status light 40. Because the reservoir status lights 40 are located closer to the reservoir scales 30 in the extracorporeal blood treatment apparatus as described herein, a user may be able to identify reservoirs 32 possibly needing replacement and/or replace those reservoirs 32 without requiring them to shift their attention away from the reservoir scales 30 during the process. For example, a reservoir status light 40 associated with a selected reservoir scale 30 is located closer to the selected reservoir scale 30 than any other reservoir scale 30 provided in the extracorporeal blood treatment apparatus. In the case of a first reservoir status light 40 associated with a first reservoir scale 30 and a second reservoir status light 40 associated with a second reservoir scale 30, the first reservoir status light 40 emits light from a location that is closer to the first reservoir scale 30 than the second reservoir scale 30.

In one or more embodiments, the reservoir status light 40 associated with a reservoir scale 30 may provide an indication that a reservoir 32 attached to the reservoir scale 30 has passed a selected weight limit as a part of monitoring the status of the reservoirs. That selected weight limit may, in the case of a reservoir 32 used to collect liquids from the extracorporeal blood treatment apparatus, be an upper limit such that passing (e.g., reaching and/or exceeding) the selected weight limit is an indication that the reservoir 32 is reaching or has reached its loading capacity and may need to be replaced with a reservoir 32 having more capacity to collect liquid. In the case of a reservoir 32 used to supply liquids to the extracorporeal blood treatment apparatus, the selected weight limit may be a lower limit such that passing (e.g., reaching and/or falling below) the selected weight limit is an indication that the reservoir 32 is reaching or has reached a level at which the reservoir 32 may need to be replaced with a fresh reservoir 32 containing additional liquid to be supplied to the extracorporeal blood treatment apparatus 1.

Figure 2:
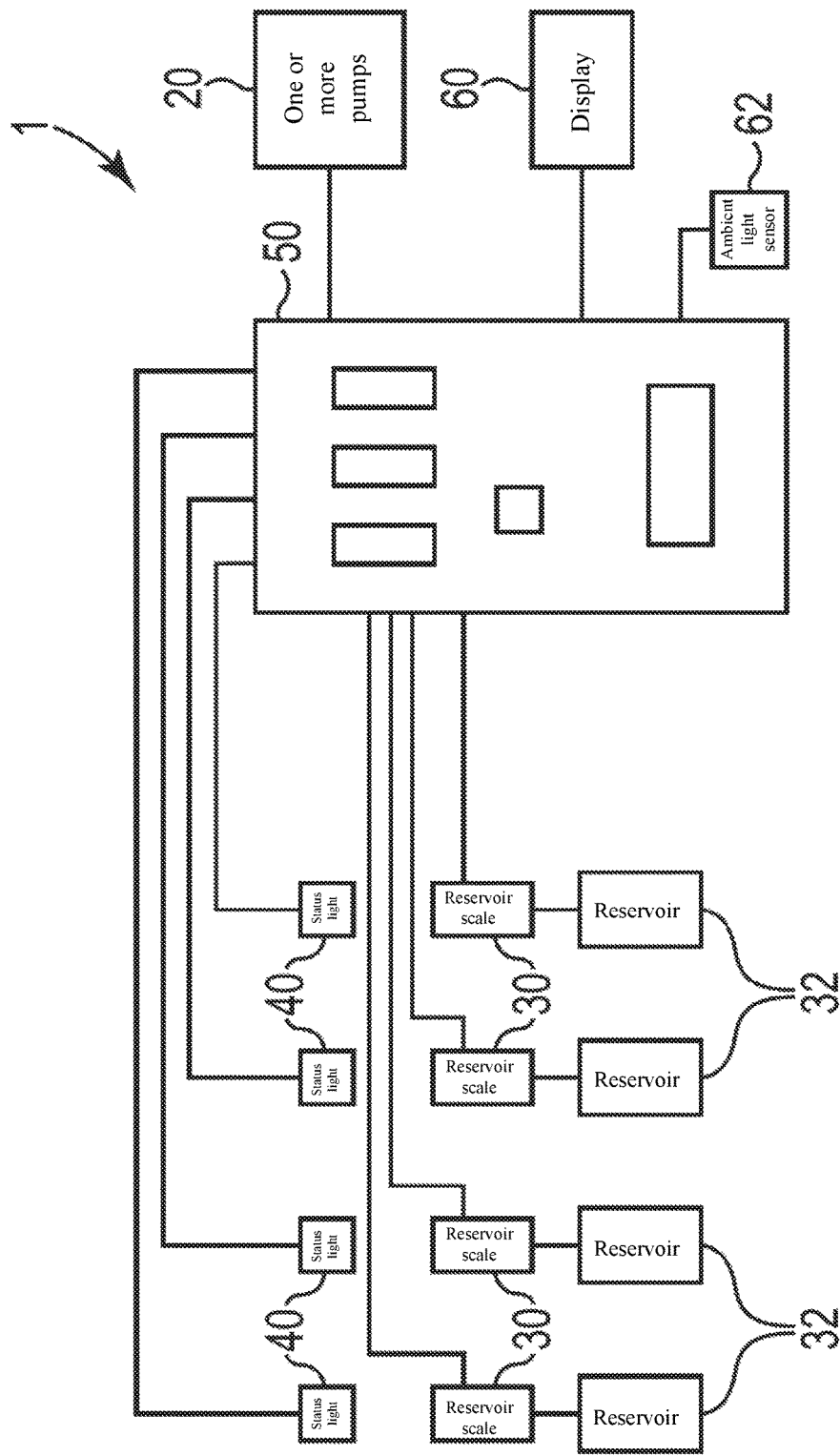
FIG. 2 is a schematic depiction of one illustrative embodiment of an extracorporeal blood treatment apparatus as described herein.

A schematic diagram of the extracorporeal blood treatment apparatus 1 depicted in FIG. 1 is provided in FIG. 2. The extracorporeal blood treatment apparatus as depicted in FIG. 2 includes a control unit 50 with the various components of the extracorporeal blood treatment apparatus connected to the control unit 50. Among the components operably connected to the control unit 50 is a pump 20. Also connected to the control unit 50 are a plurality of reservoir scales 30. Although not connected to the control unit 50, reservoirs 32 are depicted as being attached to reservoir scales 30 in FIG. 2. Also attached to the control unit 50 are reservoir status lights 40. The schematic diagram of FIG. 2 also includes display 60 connected to the control unit 50, as well as an ambient light sensor 62.

The control units used in the extracorporeal blood treatment apparatus described herein may be provided in any suitable form and may, for example, include memory and a controller. The controller may, for example, be in the form of one or more microprocessors, Application Specific Integrated Circuit (ASIC) state machines, etc. The control units may include one or more of any suitable input devices configured to allow a user to operate the apparatus (e.g., keyboards, touchscreens, mice, trackballs, etc.), as well as display devices configured to convey information to a user (e.g., monitors (which may or may not be touchscreens), indicator lights, etc.).

The control unit 50 used in the extracorporeal blood treatment apparatus 1 may, in one or more embodiments, be configured to receive a weight signal from each reservoir scale 30, with the weight signal from each reservoir scale 30 being indicative of the weight of a reservoir 32 attached to the reservoir scale 30. The control unit 50 may further be configured to make a determination that the reservoir 32 attached to the reservoir scale 30 from which the weight signal has been received has passed a selected weight limit at least partially based on the weight signal received from the reservoir scale 30. As discussed herein, the selected weight limit may be an upper limit or a lower limit depending on whether the reservoir is used to supply liquid or collect liquid from the extracorporeal blood treatment apparatus 1. If the control unit 50 makes a determination that the reservoir 32 associated with the reservoir scale 30 has passed the selected weight limit, the control unit 50 may further be configured to change a mode of light emitted by the reservoir status light 40 associated with the reservoir scale 30.

The control unit 50 is descried herein as being, in one or more embodiments, configured to make a determination that the reservoir 32 attached to the reservoir scale 30 from which the weight signal has been received has passed a selected weight limit at least partially based on the weight signal received from the reservoir scale 30. That determination is described as being made "at least partially based on the weight signal" because, in one or more embodiments, the determination that a weight limit has been passed and/or that a reservoir requires attention or replacement may be based on factors in addition to the weight signal, e.g., flow into or out of a reservoir 32 as measured using a pump 20 or other component of the extracorporeal blood treatment apparatus, etc.

In one or more embodiments of the extracorporeal blood treatment apparatus described herein, the control unit 50 may further be configured to make a determination that a second reservoir 32 attached to a second reservoir scale 30 has passed a selected weight limit at least partially based on the weight signals received from the second reservoir scale 30. If the control unit 50 makes a determination that the reservoir 32 attached to the second reservoir scale 30 has passed the selected weight limit for that reservoir scale, the control unit 50 may further be configured to change a mode of light emitted by the reservoir status light 40 associated with the second reservoir scale 30.

In the extracorporeal treatment apparatus described herein, changing the mode of light emitted by one of the reservoir status lights 40 can take a variety of different forms. For example, in one or more embodiments, changing the mode of light may involve varying the intensity of light emitted by the reservoir status light 40 with the variation in intensity being manifested by, e.g., a change in brightness. In one or more embodiments, varying the intensity of light emitted by a reservoir status light 40 can take the form of turning the reservoir status light 40 on and off such that it blinks. In one or more alternative embodiments, varying the intensity of light may involve blinking a reservoir status light 40 at one or more different rates, i.e., varying the amount of time the light is on and/or off such that the rate of blinking changes.

In one or more embodiments, changing the mode of light emitted by one of the reservoir status lights 40 can take the form of changing the color of light emitted by the reservoir status light 40 in place of or in addition to changing the intensity of the light emitted by the reservoir status light 40. These and many other variations can be envisioned as part of changing the mode of light emitted by one of the reservoir status lights 40 in an extracorporeal blood treatment apparatus as described herein.

In one or more embodiments of the extracorporeal blood treatment apparatus described herein, the control unit 50 may also be configured to make a determination that the weight of liquid in a reservoir 32 attached to a reservoir scale 30 has not passed a selected weight limit for that reservoir scale 30. If it is determined that the weight of the liquid in the reservoir 32 has not passed the selected weight limit, the control unit 50 may further be configured to cause the reservoir status light 40 associated with the reservoir scale 32 emit light of a selected color. In one or more embodiments, that selected color emitted by the reservoir status light 40 may match the color of the passive color indicator 34 associated with the reservoir scale 30.

Because the extracorporeal blood treatment apparatus described herein include a plurality of reservoir scales 30 to which reservoirs 32 are attached and those reservoir scales 30 are each associated with one or more different reservoir status lights 40, the selected colors emitted by the reservoir status lights 40 associated with different reservoir scales 30 may be different, e.g., one reservoir status light 40 may emit yellow light while a different reservoir status light 40 may emit blue light, etc.

As discussed herein, one or more embodiments of the extracorporeal blood treatment apparatus described herein may include a display screen 60 connected to a control unit 50. The extracorporeal blood treatment apparatus may also include an ambient light sensor 62 that is operably connected to the control unit 50 which may be configured to reduce the intensity of light emitted from the display screen 60 when the level of ambient light detected by the ambient light sensor 62 is below a selected ambient light threshold. In extracorporeal blood treatment apparatus that include these features, the display screen 60 may, in one or more embodiments, automatically dim in a darkened room. Although the ability of a person to monitor the status of the reservoirs 32 attached to the extracorporeal blood treatment apparatus using the display screen 60 may be impaired if the display screen 60 is dimmed, the addition of reservoir status lights 40 may allow a person to monitor the status of the reservoirs 32 even though the display screen 60 is too dim to accurately do so. In one or more embodiments of the extracorporeal blood treatment apparatus described herein, the brightness of the display screen 60 may be increased if the intensity of the light detected by the ambient light sensor 62 indicates that the amount of ambient light in the room has increased to a level that warrants an increase in the display brightness.

The reservoir scales used to hold and weigh reservoirs used in the extracorporeal blood treatment apparatus described herein may take any number of a variety of different forms. Examples of some potentially suitable reservoir scales and associated structure may be found in International Publication WO 2004/069311 and U.S. Pat. No. 7,891,625, as well as the reservoir scales and hangers used in some commercially available hemodialysis machines (e.g., PRISMAFLEX machines available from Gambro Lundia AB, etc.).

In one or more embodiments, the reservoir scales used in the extracorporeal blood treatment apparatus described herein may have a loading position and an operating position. In particular, the reservoir scales may have a loading position in which it is easier or more convenient to remove and or attach a reservoir to the reservoir scale and an operating position in which the reservoir scale is in a position and/or location that provides for accurate weighing of a reservoir attached to the reservoir scale.

Figure 3:
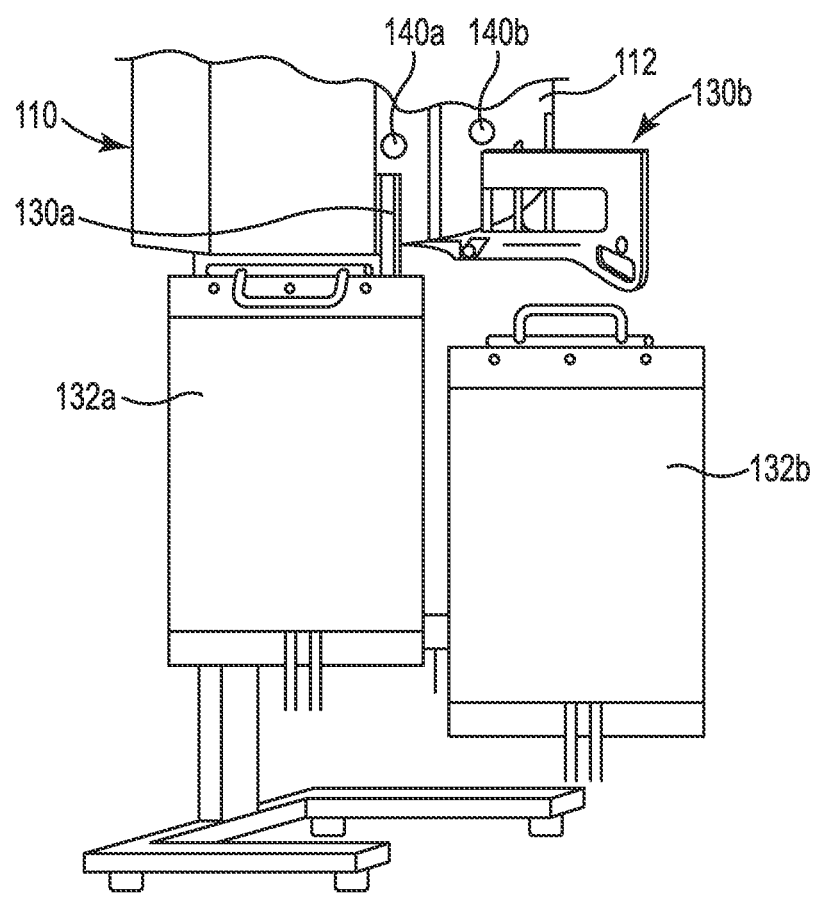
FIG. 3 is a partial perspective view of an alternative illustrative embodiment of an extracorporeal blood treatment apparatus including one reservoir scale in a loading position and one reservoir scale having a reservoir attached thereto and in an operating position.

Referring to FIG. 3, a partial view of one alternative illustrative embodiment of an extracorporeal blood treatment apparatus as described herein is depicted. The apparatus includes a housing 110 having a front face 112. The extracorporeal blood treatment apparatus includes a plurality of reservoir scales and of those reservoir scales, reservoir scale 130*a* (including an attached reservoir 132*a*) is in an operating position which, in the depicted embodiment, means that the reservoir scale 130*a* is advanced into and retained within the housing 110. Another reservoir scale 130*b* is depicted in FIG. 3 in a loading position which, in the depicted embodiment, means that the reservoir scale 130*b* has been pulled out of or extends from the front face 112 of the housing 110 of the extracorporeal blood treatment apparatus so that the reservoir 132*b* can be attached to reservoir scale 130*b*.

Also depicted in FIG. 3 is a reservoir status light 140*a* that is associated with reservoir scale 130*a* and a reservoir status light 140*b* that is associated with reservoir scale 130*b*. In one or more embodiments of the extracorporeal blood treatment apparatus described herein, the reservoir status light 140*a* may emit light in an operating mode as an indication that its associated reservoir scale 130*a* is in its operating position. Also in one or more embodiments of the extracorporeal blood treatment apparatus described herein, the reservoir status light 140*b* may emit light in a loading mode as an indication that associated reservoir scale 130*b* is in its loading position.

In extracorporeal blood treatment apparatus that include a control unit to which the reservoir scales 130*a* and 130*b* as well as the reservoir status lights 140*a* and 140*b* are operably attached, the control unit may be configured to cause the reservoir status lights 140*a* and 140*b* to emit light in either of the operating mode or the loading mode depending on the status of the reservoir scales. Determination of the status of the reservoir scales, i.e., whether they are in an operating position or a loading position, may be accomplished using any number of techniques, e.g. position sensors in the form of, e.g., proximity sensors, photocells, etc.

In extracorporeal blood treatment apparatus as described herein including reservoir status lights that emit light of a selected color that may match a passive color indicator on a reservoir scale associated with the reservoir status light, the light emitted by the reservoir status light in the operating mode may, in one or more embodiments, be of the selected color. As a result, when the reservoir scale associated with a reservoir status light is in the operating position and the weight of liquid in a reservoir attached to the reservoir scale has not passed the selected weight limit, the reservoir status light will emit operating mode light of the selected color and that selected color may, in one or more embodiments, match a passive color indicator associated with the reservoir scale as described herein.

Further, in one or more embodiments of the extracorporeal blood treatment apparatus described herein, the reservoir status lights may emit light of one selected loading mode color when the reservoir scale associated with each reservoir status light is in the loading position. That selected loading mode color may, in one or more embodiments, be the same across all reservoir status lights used in the extracorporeal blood treatment apparatus.

Figure 4:
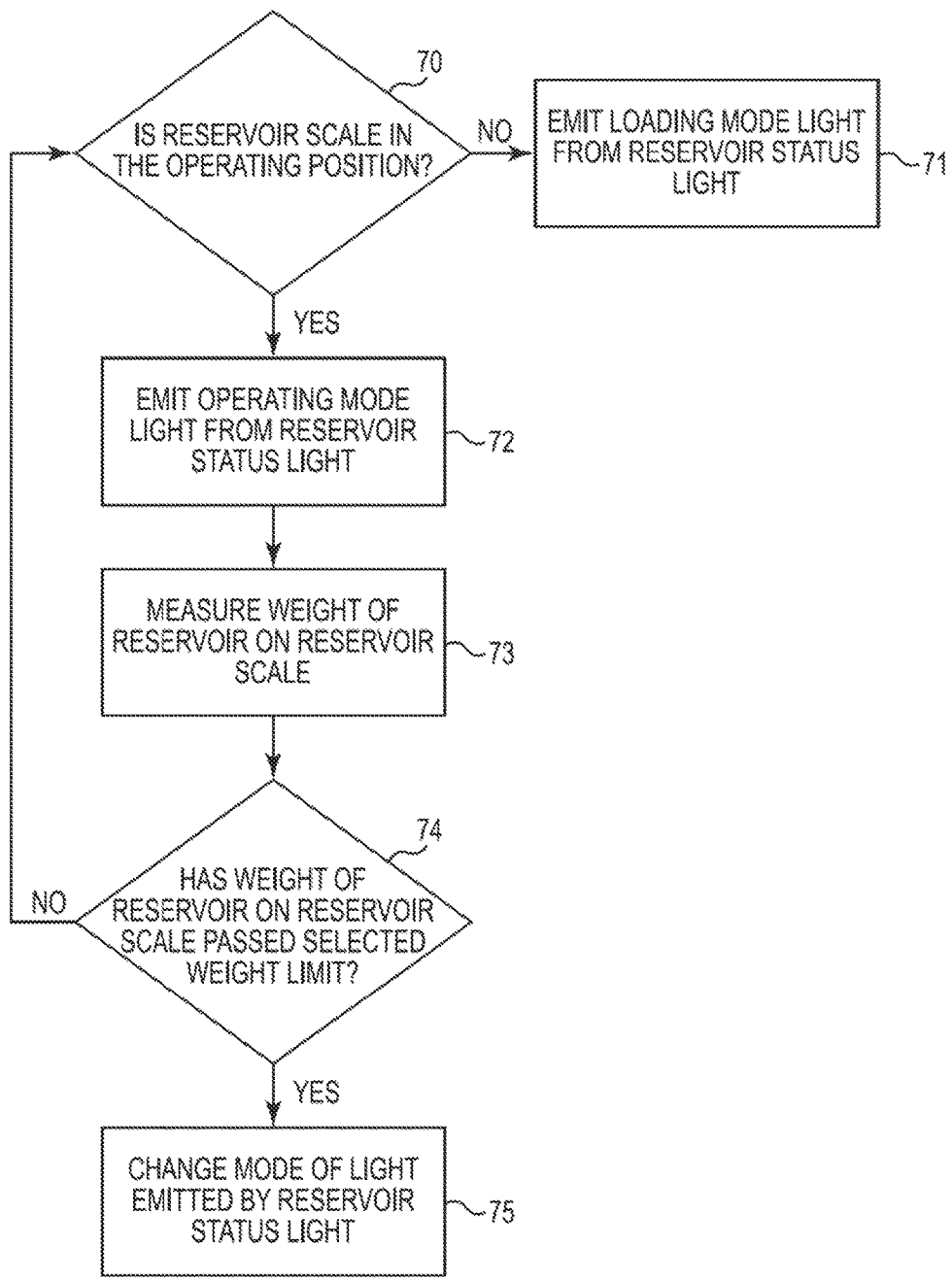
FIG. 4 is a flowchart of one illustrative embodiment of a method of operating an extracorporeal blood treatment apparatus as described herein.

Although methods of monitoring reservoir status in an extracorporeal blood treatment apparatus are described in connection with the apparatus depicted in FIGS. 1-3, one or more embodiments of the methods of monitoring reservoir status as described herein may include the steps depicted in the flowchart of FIG. 4. The illustrative embodiment of the method depicted in the flowchart of FIG. 4 includes determining whether a reservoir scale is in the operating position 70. If the reservoir scale is not in its operating position, the method may, in one or more embodiments, involve making a determination that the reservoir scale is in a loading position and a reservoir status light associated with the reservoir scale may emit loading mode light 71. Alternatively, if the determination has been made that the reservoir scale is in the operating position, then the reservoir status light associated with the reservoir scale may emit operating mode light 72.

If a determination is made that the reservoir scale is in the operating position 70 and the reservoir status light is emitting operating mode light 72, one or more embodiments of the methods described herein may include measuring the weight of the reservoir on the reservoir scale 73. The weight of the reservoir on the reservoir scale is then used to make a determination as to whether or not weight of the reservoir on the reservoir scale has passed the selected weight limit 74.

If the weight of the reservoir attached to a reservoir scale has passed the selected weight limit, the method may further include changing the mode of light emitted by the reservoir status light 75 associated with that reservoir scale. As described herein, changing the mode of light emitted by a reservoir status light may involve, e.g., changes in intensity, color, etc.

If the weight of the reservoir attached to a reservoir scale has not passed selected weight limit, the method may include further determinations with respect to whether or not the reservoir scale is in the operating position 70 followed by the subsequent steps as described above until a determination is made that the reservoir attached to the reservoir scale has passed the selected weight limit.

In one or more embodiments of the methods described herein, the color of light emitted by a reservoir status light associated with a particular reservoir scale may match the color of a passive color indicator that is either located on the reservoir scale or located nearby so as to be associated with the reservoir scale as described herein.

In one or more embodiments of the methods described herein, the intensity of light emitted from a display screen on the extracorporeal blood treatment apparatus may be reduced when light detected by an ambient light sensor is below a selected ambient light threshold.

Illustrative embodiments of the extracorporeal blood treatment apparatus and methods of monitoring the status of reservoirs used in the extracorporeal blood treatment apparatus are discussed herein some possible variations have been described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An extracorporeal blood treatment apparatus comprising:
   a housing comprising a front face and a bottom end;
   one or more pumps located on or in the housing, wherein the one or more pumps are configured to move blood and a treatment solution during extracorporeal blood treatment, wherein the one or more pumps are located above the bottom end of the housing;
   a plurality of reservoir scales positioned proximate the bottom end of the housing, wherein each reservoir scale of the plurality of reservoir scales is configured to weigh a reservoir operably attached to the reservoir scale, wherein the reservoir is positioned below the bottom end of the housing, and wherein the plurality of reservoir scales comprises at least a first reservoir scale and a second reservoir scale;
   a plurality of reservoir status lights, wherein each reservoir status light of the plurality of reservoir status lights is associated with one reservoir scale of the plurality of reservoir scales, and wherein the plurality of reservoir status lights comprises a first reservoir status light associated with the first reservoir scale and a second reservoir status light associated with the second reservoir scale, and further wherein the first reservoir status light emits light from a location that is closer to the first reservoir scale than the second reservoir scale;
   a control unit operably attached to the one or more pumps, the plurality of reservoir scales, and the plurality of reservoir status lights, wherein the control unit is configured to:
      receive a weight signal from each reservoir scale of the plurality of reservoir scales, wherein the weight signal from each reservoir scale is indicative of a weight of a reservoir operably attached to the reservoir scale;
      make a determination that a reservoir operably attached to the first reservoir scale has passed a first selected weight limit at least partially based on the weight signal received from the first reservoir scale;
      change a mode of light emitted by the first reservoir status light after making the determination that the first reservoir scale has passed the first selected weight limit;
      make a determination that a reservoir operably attached to the second reservoir scale has passed a second selected weight limit at least partially based on the weight signal received from the second reservoir scale;
      change a mode of light emitted by the second reservoir status light after making the determination that the second reservoir scale has passed the second selected weight limit;
      make a determination that the weight of liquid in the reservoir operably attached to the first reservoir scale has not passed the first selected weight limit;
      cause the first reservoir status light to emit light of a first color when the weight of liquid in the reservoir operably attached to the first reservoir scale has not passed the first selected weight limit;
      make a determination that the weight of liquid in the reservoir operably attached to the second reservoir scale has not passed the second selected weight limit;
      cause the second reservoir status light to emit light of a second color when the weight of liquid in the reservoir operably attached to the second reservoir scale has not passed the second selected weight limit, wherein the first color and the second color are different colors.

2. An apparatus according to claim 1, wherein the first reservoir status light is located on the first reservoir scale and the second reservoir status light is located on the second reservoir scale.

3. An apparatus according to claim 1, wherein the first reservoir status light is located on the housing proximate the first reservoir scale and the second reservoir status light is located on the housing proximate the second reservoir scale.

4. An apparatus according to claim 1, wherein the first reservoir scale comprises a loading position in which the first reservoir scale is configured to receive a reservoir operably attached to the first reservoir scale, and an operating position in which the first reservoir scale is configured to weigh a reservoir operably attached to the first reservoir scale during operation of the extracorporeal blood treatment apparatus, and wherein the control unit is configured to cause the first reservoir status light to emit light in an operating mode when the first reservoir scale is in the operating position.

5. An apparatus according to claim 4, wherein the control unit is configured to cause the first reservoir status light to emit light in a loading mode when the first reservoir scale is not in the operating position.

6. An apparatus according to claim 1, wherein the apparatus comprises a first passive color indicator on the housing and/or the first reservoir scale, wherein the first passive color indicator matches the first color emitted by the first reservoir status light when the weight of liquid in the reservoir operably attached to the first reservoir scale has not passed the first selected weight limit, and wherein the apparatus comprises a second passive color indicator on the second reservoir scale, wherein the second passive color indicator matches the second color emitted by the second reservoir status light when the weight of liquid in the reservoir operably attached to the second reservoir scale has not passed the second selected weight limit.

7. An apparatus according to claim 1, wherein changing the mode of light emitted by the first reservoir status light after making the determination that the first reservoir scale has passed the first selected weight limit comprises causing the first reservoir status light to vary the intensity of light emitted by the first reservoir status light.

8. An apparatus according to claim 1, wherein changing the mode of light emitted by the first reservoir status light after making the determination that the first reservoir scale has passed the first selected weight limit comprises causing the first reservoir status light to change the color of light emitted by the first reservoir status light.

9. An apparatus according to claim 1, wherein changing the mode of light emitted by the second reservoir status light after making the determination that the second reservoir scale has passed the second selected weight limit comprises causing the second reservoir status light to vary the intensity of light emitted by the second reservoir status light.

10. An apparatus according to claim 1, wherein changing the mode of light emitted by the second reservoir status light after making the determination that the second reservoir scale has passed the second selected weight limit comprises causing the second reservoir status light to change the color of light emitted by the second reservoir status light.

11. An apparatus according to claim 1, wherein the apparatus comprises a display screen operably connected to the control unit and an ambient light sensor operably connected to the control unit, and wherein the control unit is configured to reduce the intensity of light emitted from the display screen when ambient light detected by the ambient light sensor is below a selected ambient light threshold.

12. A method of monitoring reservoir status in an extracorporeal blood treatment apparatus that comprises one or more pumps located on or in a housing that are configured to move blood and a treatment solution during extracorporeal blood treatment, a first reservoir scale and a second reservoir scale positioned proximate a bottom end of the housing, and a first reservoir status light associated with the first reservoir scale and a second reservoir status light associated with the second reservoir scale, the method comprising:
receiving a weight signal from the first reservoir scale, wherein the weight signal from the first reservoir scale is indicative of a weight of a reservoir operably attached to the first reservoir scale;
determining that a reservoir operably attached to the first reservoir scale has passed a first selected weight limit at least partially based on the weight signal received from the first reservoir scale;
changing a mode of light emitted by the first reservoir status light after determining that the first reservoir scale has passed the first selected weight limit, wherein the first reservoir status light emits light from a location that is closer to the first reservoir scale than the second reservoir scale;
determining that a reservoir operably attached to the second reservoir scale has passed a second selected weight limit at least partially based on the weight signal received from the second reservoir scale; and
changing a mode of light emitted by the second reservoir status light after determining that the second reservoir scale has passed the second selected weight limit;
determining that the weight of liquid in the reservoir operably attached to the first reservoir scale has not passed the first selected weight limit;
emitting light of a first color from the first reservoir status light of a first color when the weight of liquid in the reservoir operably attached to the first reservoir scale has not passed the first selected weight limit;
determining that the weight of liquid in the reservoir operably attached to the second reservoir scale has not passed the second selected weight limit; and
emitting light of a second color from the second reservoir status light when the weight of liquid in the reservoir operably attached to the second reservoir scale has not passed the second selected weight limit, wherein the first color and the second color are different colors.

13. A method according to claim 12, wherein the first reservoir scale comprises a loading position in which the first reservoir scale is configured to receive a reservoir operably attached to the first reservoir scale, and an operating position in which the first reservoir scale is configured to weigh a reservoir operably attached to the first reservoir scale during operation of the extracorporeal blood treatment apparatus, and wherein the method further comprises:
emitting light from the first reservoir status light in a loading mode when the first reservoir scale is not in the operating position; and
emitting light from the first reservoir status light in an operating mode when the first reservoir scale is in the operating position, wherein the light emitted from the first reservoir status light in the loading mode differs from the light emitted from the first reservoir status light in the operating mode.

14. A method according to claim 12, wherein the first reservoir status light is located on the first reservoir scale and the second reservoir status light is located on the second reservoir scale.

15. A method according to claim 12, wherein the first reservoir status light is located on the housing proximate the first reservoir scale and the second reservoir status light is located on the housing proximate the second reservoir scale.

16. A method according to claim 12, wherein the apparatus comprises a first passive color indicator on the housing and/or the first reservoir scale and a second passive color indicator on the housing and/or the second reservoir scale;
wherein the light of the first color emitted by the first reservoir status light matches the first passive color indicator when the weight of liquid in the reservoir operably attached to the first reservoir scale has not passed the first selected weight limit;
and wherein the light of the second color emitted by the second reservoir status light matches the second passive color indicator when the weight of liquid in the reservoir operably attached to the second reservoir scale has not passed the second selected weight limit.

17. A method according to claim 12, wherein changing the mode of light emitted by the first reservoir status light after determining that the first reservoir scale has passed the first selected weight limit comprises varying the intensity of light emitted by the first reservoir status light.

18. A method according to claim 12, wherein changing the mode of light emitted by the first reservoir status light after determining that the first reservoir scale has passed the first selected weight limit comprises changing the color of light emitted by the first reservoir status light.

19. A method according to claim 12, wherein changing the mode of light emitted by the second reservoir status light after determining that the second reservoir scale has passed the second selected weight limit comprises varying the intensity of light emitted by the second reservoir status light.

20. A method according to claim 12, wherein changing the mode of light emitted by the second reservoir status light after determining that the second reservoir scale has passed the second selected weight limit comprises changing the color of light emitted by the second reservoir status light.

21. A method according to claim 12, wherein the apparatus comprises a display screen and an ambient light sensor, and wherein the method further comprises reducing the intensity of light emitted from the display screen when ambient light detected by the ambient light sensor is below a selected ambient light threshold.

22. An extracorporeal blood treatment apparatus comprising:
- a housing comprising a front face and a bottom end;
- one or more pumps located on or in the housing, wherein the one or more pumps are configured to move blood and a treatment solution during extracorporeal blood treatment, wherein the one or more pumps are located above the bottom end of the housing;
- a plurality of reservoir scales positioned proximate the bottom end of the housing, wherein each reservoir scale of the plurality of reservoir scales is configured to weigh a reservoir operably attached to the reservoir scale, wherein the reservoir is positioned below the bottom end of the housing, and wherein the plurality of reservoir scales comprises at least a first reservoir scale and a second reservoir scale;
- a plurality of reservoir status lights, wherein each reservoir status light of the plurality of reservoir status lights is associated with one reservoir scale of the plurality of reservoir scales, and wherein the plurality of reservoir status lights comprises a first reservoir status light associated with the first reservoir scale and a second reservoir status light associated with the second reservoir scale, and further wherein the first reservoir status light emits light from a location that is closer to the first reservoir scale than the second reservoir scale, wherein the first reservoir status light is located on the housing proximate the first reservoir scale and the second reservoir status light is located on the housing proximate the second reservoir scale;
- a control unit operably attached to the one or more pumps, the plurality of reservoir scales, and the plurality of reservoir status lights, wherein the control unit is configured to:
  - receive a weight signal from each reservoir scale of the plurality of reservoir scales, wherein the weight signal from each reservoir scale is indicative of a weight of a reservoir operably attached to the reservoir scale;
  - make a determination that a reservoir operably attached to the first reservoir scale has passed a first selected weight limit at least partially based on the weight signal received from the first reservoir scale;
  - change a mode of light emitted by the first reservoir status light after making the determination that the first reservoir scale has passed the first selected weight limit;
  - make a determination that the weight of liquid in the reservoir operably attached to the first reservoir scale has not passed the first selected weight limit;
  - cause the first reservoir status light to emit light of a first color when the weight of liquid in the reservoir operably attached to the first reservoir scale has not passed the first selected weight limit;
  - make a determination that the weight of liquid in the reservoir operably attached to the second reservoir scale has not passed the second selected weight limit; and
  - cause the second reservoir status light to emit light of a second color when the weight of liquid in the reservoir operably attached to the second reservoir scale has not passed the second selected weight limit, wherein the first color and the second color are different colors;
  - make a determination that the weight of liquid in the reservoir operably attached to the second reservoir scale has not passed the second selected weight limit;
  - cause the second reservoir status light to emit light of a second color when the weight of liquid in the reservoir operably attached to the second reservoir scale has not passed the second selected weight limit, wherein the first color and the second color are different colors;
- a first passive color indicator on the housing and/or the first reservoir scale, wherein the first passive color indicator matches the first color emitted by the first reservoir status light when the weight of liquid in the reservoir operably attached to the first reservoir scale has not passed the first selected weight limit;
- a second passive color indicator on the housing and/or the second reservoir scale, wherein the second passive color indicator matches the second color emitted by the second reservoir status light when the weight of liquid in the reservoir operably attached to the second reservoir scale has not passed the second selected weight limit.

23. An apparatus according to claim 22, wherein the first reservoir scale comprises a loading position in which the first reservoir scale is configured to receive a reservoir operably attached to the first reservoir scale, and an operating position in which the first reservoir scale is configured to weigh a reservoir operably attached to the first reservoir scale during operation of the extracorporeal blood treatment apparatus, and wherein the control unit is configured to:
- cause the first reservoir status light to emit light in an operating mode when the first reservoir scale is in the operating position, and
- cause the first reservoir status light to emit light in a loading mode when the first reservoir scale is not in the operating position, wherein the operating mode and the loading mode are different.

24. An apparatus according to claim 22, wherein the first color is indicative of liquid in the reservoir operably attached to the first reservoir scale and the second color is indicative of liquid in the reservoir operably attached to the second reservoir scale.

25. A method according to claim 12, wherein the first color is indicative of liquid in the reservoir operably attached to the first reservoir scale and the second color is indicative of liquid in the reservoir operably attached to the second reservoir scale.

* * * * *

UNITED STATES PATENT AND TRADEMARK OFFICE
CERTIFICATE OF CORRECTION

PATENT NO. : 10,052,425 B2
APPLICATION NO. : 14/774004
DATED : August 21, 2018
INVENTOR(S) : John O'Mahony Page 1 of 1

It is certified that error appears in the above-identified patent and that said Letters Patent is hereby corrected as shown below:

Page 5, Column 2, under Line 40, Foreign Patent Documents, insert --WO WO 2004/69311 8/2004--

Signed and Sealed this
Sixteenth Day of April, 2019

Andrei Iancu
*Director of the United States Patent and Trademark Office*